(12) United States Patent
Graf et al.

(10) Patent No.: US 7,377,912 B2
(45) Date of Patent: May 27, 2008

(54) LATCHING BLOCK FOR CONNECTING CASING SECTIONS OF AN ADMINISTERING APPARATUS

(75) Inventors: Roney Graf, Burgdorf (CH); Fritz Kirchhofer, Sumiswald (CH)

(73) Assignee: TecPharma Licensing AG, Burgdorf (CH)

( * ) Notice: Subject to any disclaimer, the term of this patent is extended or adjusted under 35 U.S.C. 154(b) by 3 days.

(21) Appl. No.: 10/767,976

(22) Filed: Jan. 29, 2004

(65) Prior Publication Data
US 2004/0215153 A1 Oct. 28, 2004

Related U.S. Application Data

(63) Continuation of application No. PCT/CH02/00409, filed on Jul. 22, 2002.

(30) Foreign Application Priority Data
Jul. 30, 2001 (DE) .......................... 201 12 501 U
Dec. 21, 2001 (DE) .............................. 101 63 325

(51) Int. Cl.
*A61M 5/00* (2006.01)
(52) U.S. Cl. ..................................... 604/208
(58) Field of Classification Search ................ 604/187, 604/207–209, 218, 220, 223, 224, 228, 232–234, 604/246, 890.1
See application file for complete search history.

(56) References Cited

U.S. PATENT DOCUMENTS

| 4,592,745 A | 6/1986 | Rex et al. |
| 4,973,318 A | 11/1990 | Holm et al. |
| 5,026,343 A * | 6/1991 | Holzer ........................ 604/68 |
| 5,226,895 A | 7/1993 | Harris |
| 5,279,585 A | 1/1994 | Balkwill |
| 5,304,152 A | 4/1994 | Sams |
| 5,383,865 A | 1/1995 | Michel |

(Continued)

FOREIGN PATENT DOCUMENTS

DE 4425763 A1 1/1996

(Continued)

*Primary Examiner*—Kevin C. Sirmons
*Assistant Examiner*—Catherine N. Witczak
(74) *Attorney, Agent, or Firm*—David E. Bruhn; Dorsey & Whitney LLP

(57) ABSTRACT

An administering apparatus for delivering a dosage of product including a casing with a reservoir for the product, a piston within the reservoir to deliver the product, a piston rod for engaging the piston, a drive device for driving the piston rod, and a dosage setting member mechanically engaging the piston rod and a stopper for the dosage setting member. The casing includes a front casing section containing a reservoir for the product and a rear casing section detachably connected to the front casing section. The front casing section is connected to or forms a first latching element, and the rear casing section is connected to or forms a second latching element. The latching elements are in latching engagement when the casing sections are connected. The casing sections may be axially fixed to one another by the latching engagement. The casing sections may alternately be fixed to one another, secured against rotating, with respect to a rotational movement about a longitudinal axis of the casing sections parallel to the advancing direction, by the latching engagement. The administering apparatus further includes a latching block coupled to the drive element such that the latching engagement can only be released in a releasing position of the drive element.

37 Claims, 9 Drawing Sheets

U.S. PATENT DOCUMENTS

| | | |
|---|---|---|
| 5,545,147 A | 8/1996 | Harris |
| 5,611,783 A * | 3/1997 | Mikkelsen .................. 604/208 |
| 5,630,796 A * | 5/1997 | Bellhouse et al. .......... 604/518 |
| 6,146,361 A | 11/2000 | Dibiasi et al. |
| 6,200,296 B1 | 3/2001 | Dibiasi et al. |
| 6,221,046 B1 * | 4/2001 | Burroughs et al. ......... 604/153 |
| 6,585,698 B1 * | 7/2003 | Packman et al. ........... 604/207 |
| 6,623,446 B1 * | 9/2003 | Navelier et al. ............... 604/68 |
| 6,899,698 B2 | 5/2005 | Sams |
| 2004/0186431 A1 | 9/2004 | Graf |
| 2004/0186441 A1 | 9/2004 | Graf |
| 2004/0186442 A1 | 9/2004 | Graf |
| 2004/0215152 A1 | 10/2004 | Kirchhofer et al. |

FOREIGN PATENT DOCUMENTS

| | | |
|---|---|---|
| EP | 0295075 A1 | 12/1988 |
| EP | 0 498 737 A1 | 8/1992 |
| EP | 0594349 A1 | 4/1994 |
| EP | 1 095 668 A1 | 5/2001 |
| WO | WO 97/17095 | 5/1997 |
| WO | WO 00/02606 | 1/2000 |

* cited by examiner

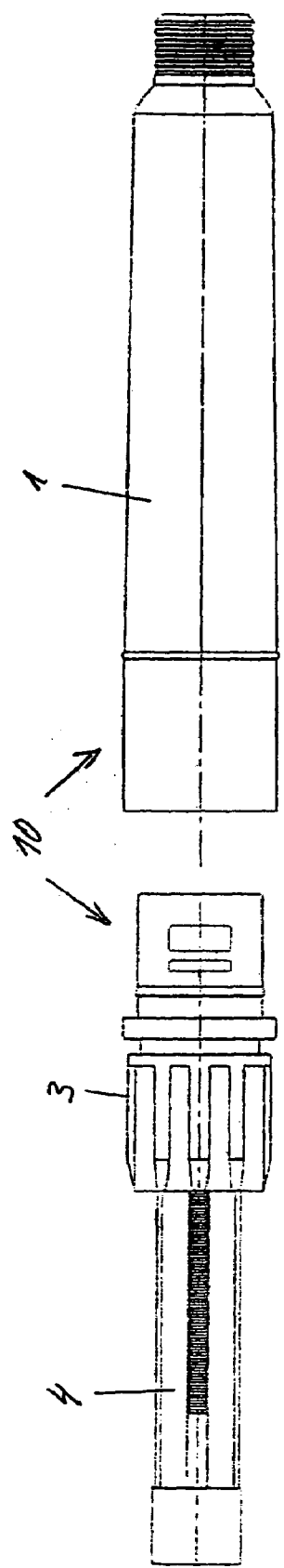
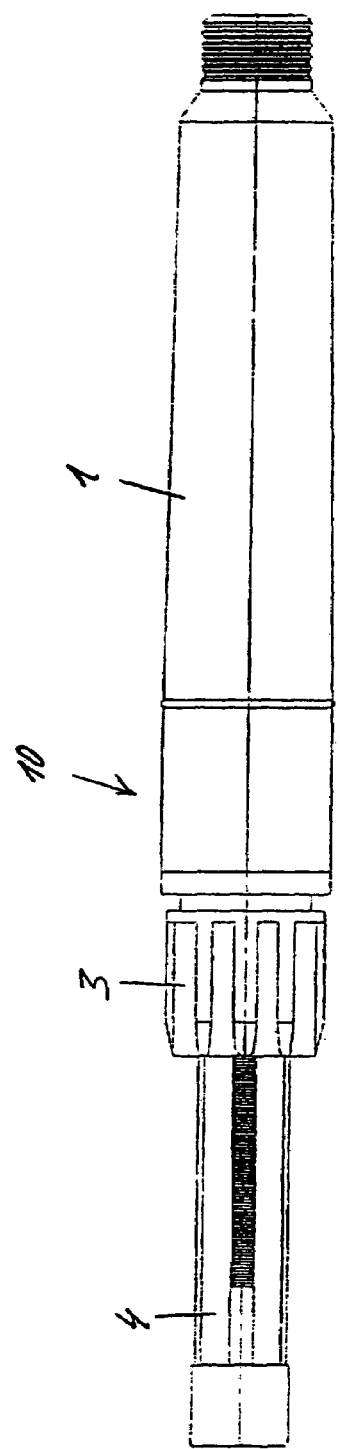
Fig. 1
Fig. 2

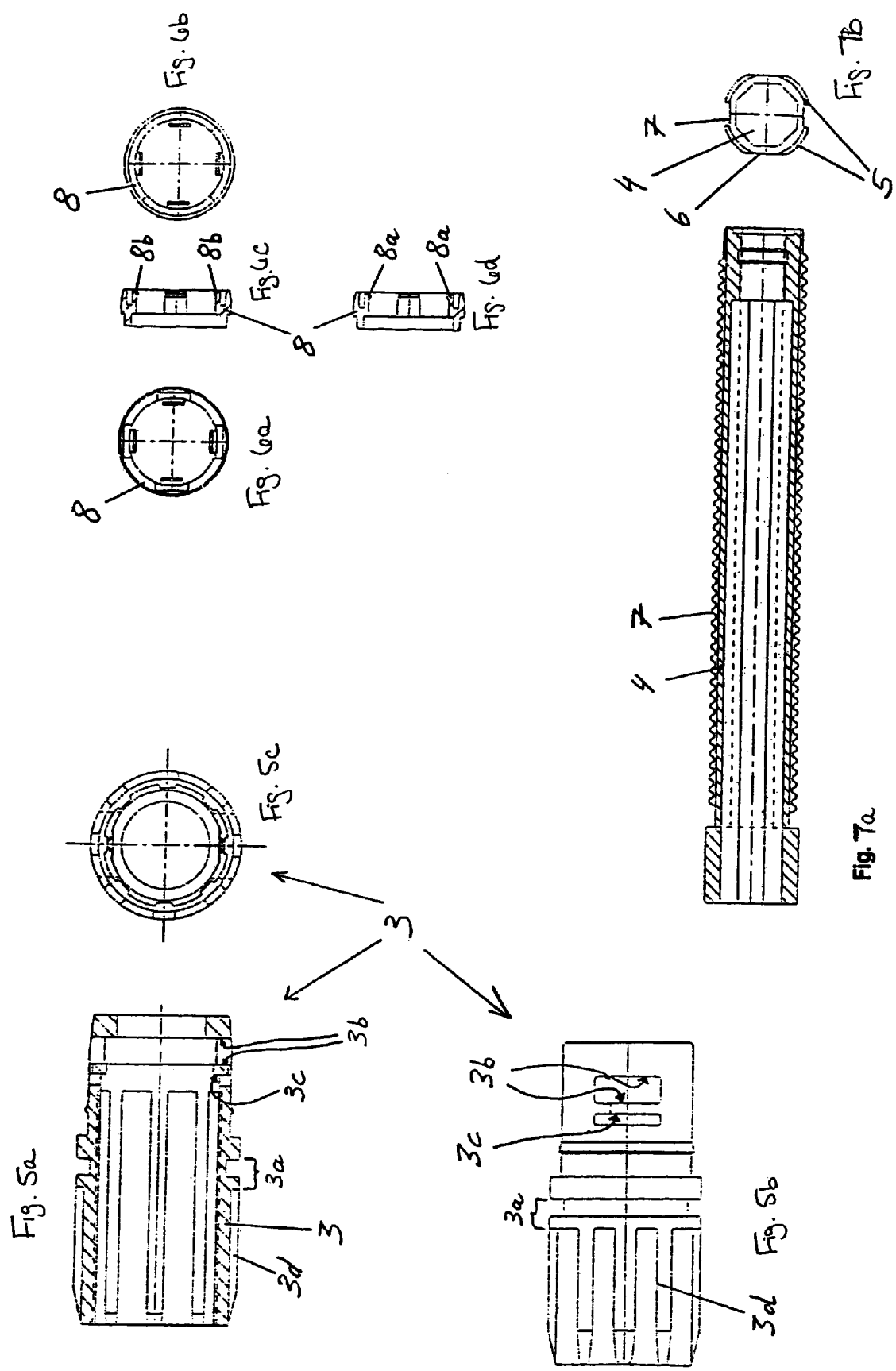

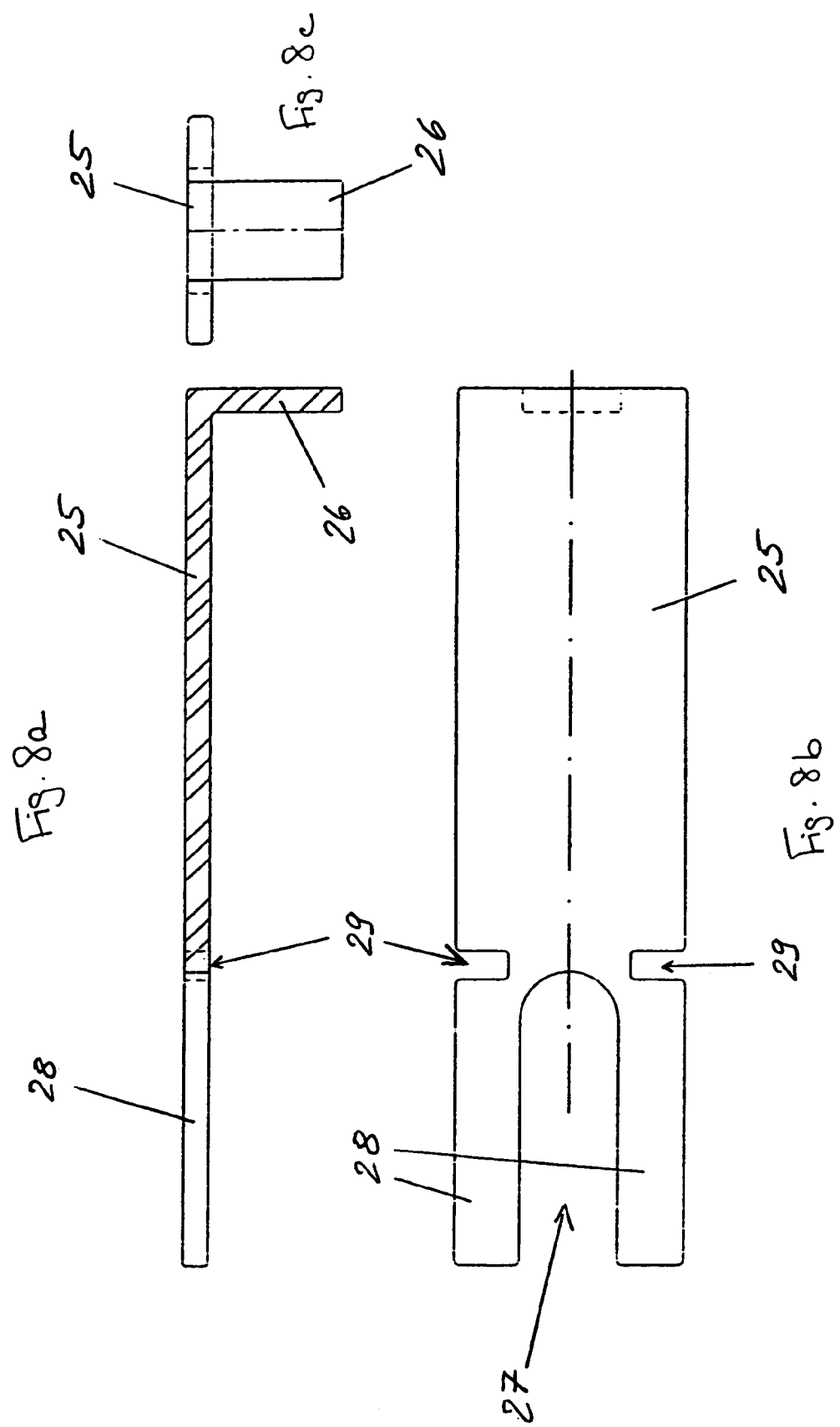

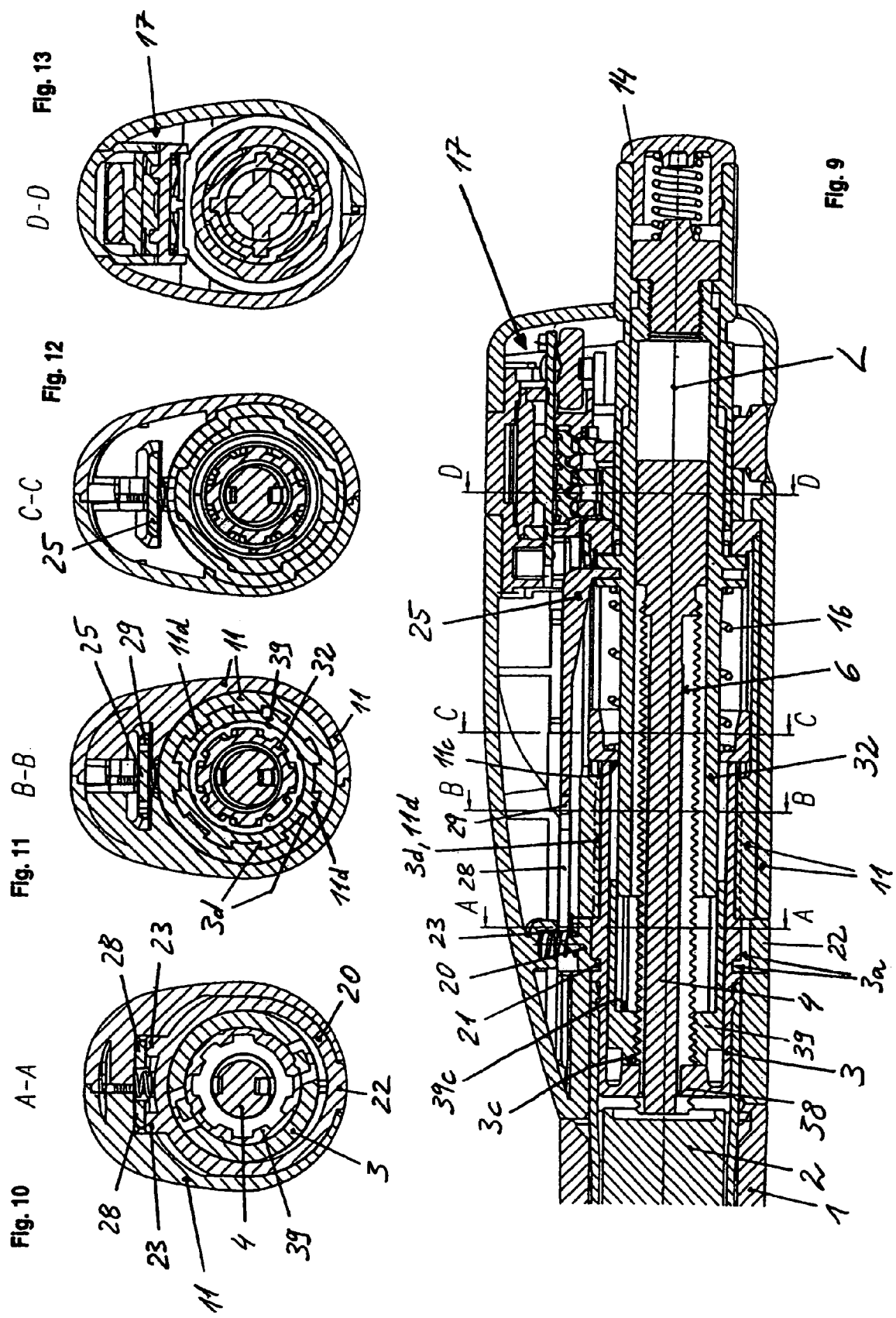

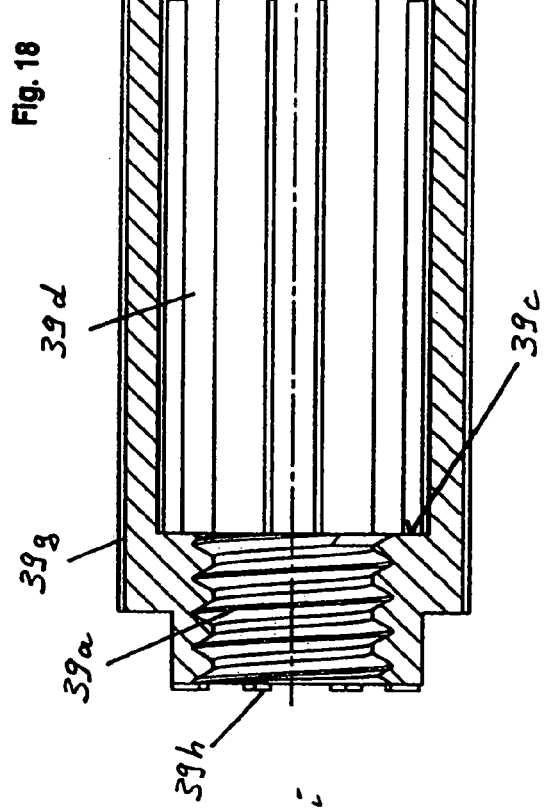
Fig. 17
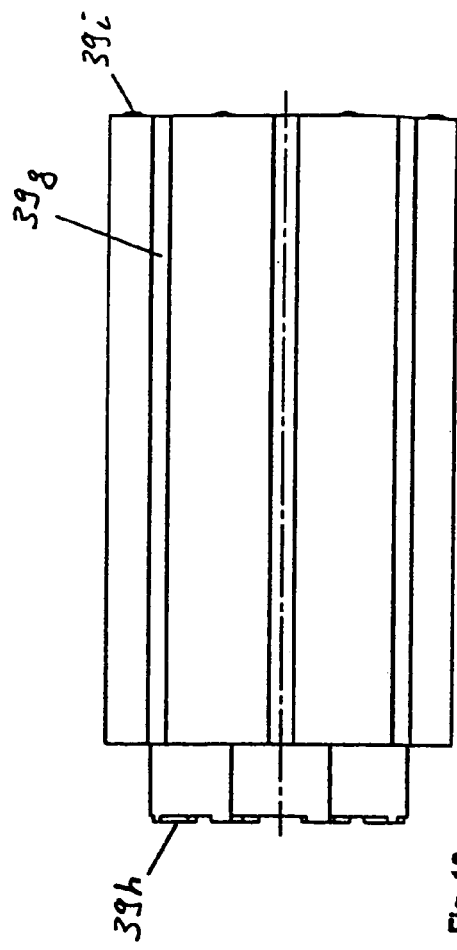
Fig. 18
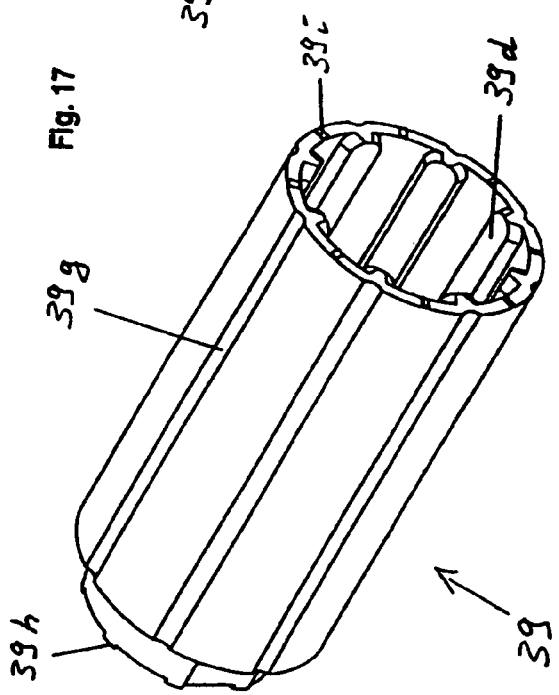
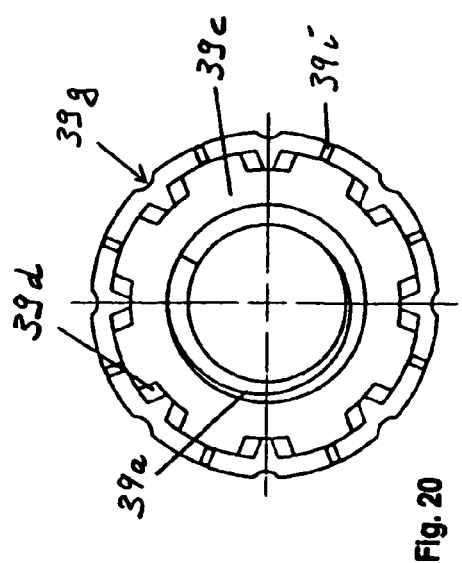
Fig. 19
Fig. 20

LATCHING BLOCK FOR CONNECTING CASING SECTIONS OF AN ADMINISTERING APPARATUS

CROSS-REFERENCE TO RELATED APPLICATIONS

This application is a Continuation of International Application No. PCT/CH02/00409, filed on Jul. 22, 2002, which claims priority to German Application No. 201 12 501.3, filed on Jul. 30, 2001, and German Application No. 101 63 325.4, filed on Dec. 21, 2001, the contents of which are incorporated herein in their entirety by reference.

BACKGROUND

The invention relates to an administering apparatus having connecting casing sections. The invention is suited to an administering apparatus having a disposable portion for one-time use and a drive device for repeated use. Such drive device may be formed as a dosing and drive device. The present invention thus may relate to, for example, a semi-disposable pens. Alternately, the invention is suited for a further type of injection apparatus, infusion apparatus, inhalation apparatus, for example wherein the product is vaporized by a vaporizing means of the inhalation apparatus, or any other suitable type of apparatus for administering a fluid product. The invention can, however, also be advantageously employed for other injection apparatus and also for infusion apparatus. It is equally advantageous for inhalation apparatus, for feeding the product to be for example vaporized by a vaporizing means of the inhalation apparatus.

An administering apparatus such as an injection apparatus or an infusion apparatus generally comprises a reservoir part for storing the product to be administered and a drive device for a single product administration or a dosing and drive device for selection and administration of the product dosage. The reservoir part contains a product reservoir, from which the product or a portion of the product is dispensed through a reservoir outlet by advancing a piston. The drive device advances the piston.

As stated above, a drive device comprising a dosing and drive device may be provided in an administering apparatus for repeated dispensation of product. The dosing and drive device typically comprises a dosing device or a portion of a dosing device and may include an indicator for optically and/or acoustically indicating the selected product dosage.

Assembly of the reservoir part with the drive device, or dosing and drive device, can be problematic as the piston in the reservoir of the reservoir part must be coupled to the drive device and possibly a dosing device or a portion of a dosing device. One problem that can arise is associated with inadvertent reuse of a used reservoir. If a used reservoir is inadvertently assembled with the reusable dosing and drive device, there is the possibility of an incorrect initial setting. An incorrect initial setting may result in an incorrect dosage being administered when the product is first administered after the apparatus has been assembled. This is particularly possible if the administering device is used for self-administration of a fluid, for example, in self-administration of insulin in diabetes therapy.

SUMMARY

The present invention provides an administering apparatus for delivering a dosage of product comprising a casing with a reservoir for the product, a piston within the reservoir to deliver the product, a piston rod for engaging the piston, a drive device for driving the piston rod, and a dosage setting member mechanically engaging the piston rod and a stopper for the dosage setting member. The casing includes a front casing section containing the reservoir for the product. The piston is positioned within the reservoir such that the piston can shift in an advancing direction towards an outlet of the reservoir to deliver the product, whether the entire product or a selected product dosage, in a piston stroke. The casing further comprises a rear casing section detachably connected to the front casing section. The front casing section is connected to or forms a first latching element, and the rear casing section is connected to or forms a second latching element. The first and second latching elements are in latching engagement when the casing sections are connected. In one embodiment, the casing sections are fixed to one another with respect to the advancing direction, i.e. axially, by the latching engagement. The casing sections may also, or alternately, be fixed to one another, secured against rotating, with respect to a rotational movement about a longitudinal axis of the casing sections parallel to the advancing direction, by the latching engagement. The connection of the casing sections may be achieved solely by the latching engagement of the first and second latching elements. Further, the first and second latching elements may form a positive lock. The administering apparatus further includes a latching block for the latching elements which is coupled to the drive element such that the latching engagement can only be released in a releasing position of the drive element.

The administering apparatus further includes a driven element, or piston rod, to move the piston in the advancing direction. The piston rod can be connected fixedly, or permanently, to the piston. Further, the piston rod may be formed with the piston as a unitary piece. In an exemplary embodiment, however, the piston and the piston rod are provided as separate components, a front end of the piston rod pushing against a rear end of the piston to deliver the product.

A drive element of a drive device, or dosing and drive device, is mounted by the rear casing such that the drive element moves in and counter to the advancing direction. The drive element is coupled to the driven element, or piston rod, such that it slaves the driven element when it moves in the advancing direction but does not slave the driven element when it retracts, counter to the advancing direction.

The administering apparatus further comprises a latching block for the latching elements. The latching block is coupled to the drive element such that the latching engagement of the latching elements is released when the latching block assumes a releasing position. The latching block retains the latching elements in latching engagement in all positions assumed by the drive element during its movement in and counter to the advancing direction, except for in the releasing position. The releasing position of the drive element may correspond to a foremost position assumed by the drive element in the advancing direction, when the apparatus is assembled.

By coupling the latching elements to the drive element in accordance with the invention, such as with the latching block, it is possible to ensure that the product dosage is selected from a state corresponding to a zero dosage. This minimizes the risk of product delivery when no dosage has been selected, for example, if the drive element was inadvertently first activated after assembling the apparatus. The coupling of the latching elements to the drive element also minimizes the risk of product in excess of the selected dosage from being delivered.

While the advantages outlined above are specific to an administering apparatus which allows product dosage selection, the administering apparatus of the present invention may alternately be one which does not allow the dosage to be selected. The administering apparatus again includes a latching mechanism and allows a product reservoir to be exchanged, for example in the form of an exchange ampoule. The product amount to be delivered is fixedly pre-set. The latching mechanism ensures that a priming process is performed when the casings are assembled.

A dosage indicator, for example an LCD display may be provided with the administering apparatus. Coupling the drive element to the latching mechanism resets the indicator to zero. While the indicator may be reset to zero mechanically, the latching block may be configured as a switch for this purpose, for example as an electronic circuit comprising the indicator.

The administering apparatus may include an infusing cannula. The cannula preferably has a diameter corresponding to or smaller than that of a 30 gauge cannula. A 31 gauge, or thinner, cannula is preferred. Cannulae with outer diameters and/or inner diameters which do not correspond to the standard ISO 9626 but whose outer diameters are not larger than that of a 30 gauge cannula also represent suitable cannulae for use with the present invention. Such cannulae are particularly suitable if the wall thicknesses are less than that specified in accordance with the standard. Although the cannula dimensions are described with respect to ISO 9626, which applies to steel cannulae, cannulae made of other bio-compatible materials are equally suitable.

The administering apparatus may enable the product dosage to be administered to be selected. In such embodiment, a dosage setting member is provided which engages with the driven element, or piston rod, such that the dosage setting member is movable in the advancing direction relative to the front and/or rear casing section and is movable counter to the advancing direction relative to the front and/or rear casing section and the piston rod. The product dosage is selected by moving the dosage setting member in the advancing direction. The dosage setting member slaves the piston rod when moving in the advancing direction. The drive element may be positioned to act on the dosage setting member. The latching engagement and the latching block ensure that when the latching engagement is established, the dosage setting member is moved into a defined position with respect to the piston. This defined position is preferably the zero position of the dosage setting member, in which the drive element cannot act on the piston via the dosage setting member.

In this embodiment, the piston rod and the dosage setting member are mounted in or by the front casing section and form a reservoir module with the front casing section. The reservoir module may be configured as a disposable module. Thus, the reservoir module may be disposed of once the reservoir is emptied. Alternately, the piston rod or dosage setting member may not be mounted by the front casing section, but rather, for example, by the rear casing section. If the piston rod and/or the dosage setting member are not mounted by the front casing, the reservoir part, comprising the front casing section and the reservoir including the piston, forms the reservoir module.

The front casing section may comprise two parts: the reservoir part and a mechanism holder. If the reservoir is an ampoule, the reservoir part is referred to as an ampoule holder. The mechanism holder mounts the piston rod and, preferably, the dosage setting member. The mechanism holder is connected to the reservoir part, secured against shifting and preferably also against rotating. The connection of the mechanism holder to the reservoir part may be detachable, for example as a screw connection, or may be non-detachable. The front casing section accommodating the reservoir may also be configured for repeated use with only the reservoir being exchanged. Similarly, the mechanism holder may be configured for repeated use. However, due to conventionally used piston rods which are secured against returning, designing a reservoir module as a disposable part has the advantage of smooth handling.

The latching engagement of the blocking elements prevents the front casing section and the rear casing section from being separated once the apparatus is assembled, other than when the drive element is in the releasing position. Further, due to the latching engagement of the blocking elements, the front casing section and the rear casing section can only be connected when the drive element is in the releasing position. This establishes a defined state, preferably the zero dosage state, or primes the apparatus, when the apparatus is assembled.

The invention thus also relates to a reservoir module comprising a front casing section having a first latching element and a drive device comprising a rear casing section having a second latching element and a drive element. The drive element may include a dosing device or a portion of a dosing device and, thus, may be configured as a dosing and drive device. A latching block may be formed in or on the drive device, but may alternately be provided in or on the reservoir module.

In any embodiment of the present invention having a first latching element and a second latching element, the first latching element and/or the second latching element may be formed as an elastic catch which is moved by elastically flexing in and out of latching engagement. The latching block allows the elastic catch to elastically flex in the releasing position of the drive element. Alternately, the first latching element and/or the second latching element movably connected to its corresponding casing section for establishing and releasing the latching engagement, may be rigid or at least sufficiently rigid that it cannot elastically and result in the latching engagement being released. In such embodiment, the moving latching element is supported against the force of an elastic restoring means, for example against the force of a pressure spring, on the corresponding casing section, such that it can move in and out of latching engagement. The movement of an elastic latching element or a non-elastic latching element is directed transverse, preferably at approximately right angles, to the advancing direction. The latching movement and the unlatching movement may be designed to point radially with respect to a central longitudinal axis of the apparatus.

The latching elements, of which at least two are provided, may be moved in and out of latching engagement. Thus, in one embodiment, first and second latching elements are formed as a male latching element and an accommodating female latching element, thereby achieving a lock/latch connection.

The latching block may comprise a blocking slider which blocks the movable latching element. If two movable latching elements are provided, the latching block may block at least one of the latching elements. The blocked latching element cannot perform an unlatching movement until the drive element assumes a releasing position. In one embodiment, the latching block is rigidly connected to the drive element, such that it participates in the movements of the drive element equally with the drive element. The drive element and the latching block may be formed as a unitary piece. Alternately, the latching block and the drive element may be formed as separate components, the latching block being connected to the drive element such that it participates equally in the movement of the drive element in and counter to the advancing direction. The blocking movement and unblocking movement of the latching block and the movement of the latching element blocked by it are preferably directed transverse, for example at approximately right angles.

While an administering apparatus in accordance with the present invention is particularly suited for movement of the drive element in the advancing direction manually performed by the user in a single motion, an administering apparatus in accordance with the present invention may be provided equally suited for performing the same movement slowly, continuously or in small increments, using motors, such as in an infusion apparatus.

The dosing and drive device of an administering apparatus in accordance with the present invention can operate manually, semi-automatically or fully automatically. For manual operation, both the rotational dosing movement and the translational delivery movement are performed manually. For semi-automatic operation, one of either the rotational dosing movement or the translational delivery movement is performed manually with the other movement being performed using motors or another type of force application, for example a spring force, when the user has triggered the corresponding movement using an activating handle. For full automatic operation, the dosing movement and the delivery movement are performed using motors or another force, for example a spring force. In this case, only the dosage is selected manually, for example using one or more buttons, and the delivery movement is triggered by the user using a corresponding activating handle. In most embodiments, the administering apparatus of the present invention is equipped with a manual dosing and drive device, which is then referred to as a dosing and activating device. Thus, whenever a "dosing and activating device" is mentioned, it is the manual embodiment which is being referred to. Where a dosing and drive device is mentioned, this is not intended to restrict the invention with respect to being manual, semi-automatic or fully automatic, but rather to comprise each of these embodiments. The term "dosing and activating module" is used in connection with all the embodiments of the dosing and drive device.

The dosing and drive device can separately comprise a dosing element which performs the dosing movement and a drive element which performs the delivery movement. Alternately, however, the dosing movement and the delivery movement are performed by the same body of the dosing and drive device which is therefore also referred to in the following as a dosing and drive element or dosing and activating element.

The product is preferably a fluid, particularly preferably a liquid, having a medical, therapeutic, diagnostic, pharmaceutical or cosmetic application. For example, the product may be insulin, a growth hormone or a thin or thick, pulpy food. The administering apparatus may be employed in applications in which a user self-administers the product him/herself, as is common in diabetes therapy. Further, use of the administering apparatus by trained staff in treating patients is not excluded.

In the case of an administering apparatus of the present invention comprising an injection apparatus, the product can be administered using an injection cannula such as a nozzle for needle-free injections. The product may be injected or infused subcutaneously, venously, or also intramuscularly. Alternately, in an embodiment of the administering apparatus of the present invention comprising an inhalation apparatus, the selected product dosage may be delivered from the reservoir into a chamber of the inhalation apparatus and vaporized for inhalation by a vaporizing means. Furthermore, oral ingestion or administration via the esophagus may be used. Alternately, the administering apparatus of the present invention may be configured for any other suitable administration to the patient.

The administering apparatus may configured as semi-disposable. In this case, the front casing section is a support for a reservoir module which is disposed of or recycled once the reservoir has been emptied. The rear casing section is a support for a dosing and activating module which may be repeatedly used in conjunction with a new reservoir module. As the reservoir module can also be treated separately as a disposable module, it is also a separate subject of the invention. Equally, a system consisting of an administering apparatus and at least one reservoir module, which can replace the reservoir module of the apparatus once it has been used, forms a subject of the invention. The duplex design of the administering apparatus, divided into a portion provided for use only once and a portion provided for repeated use (semi-disposable), is advantageous for injection pens in particular, but is also useful for other administration such as via inhalation, oral ingestion, or artificial feeding.

BRIEF DESCRIPTION OF THE DRAWINGS

FIG. 1 illustrates two portions of a reservoir module in accordance with a first embodiment of the present invention;

FIG. 2 illustrates the reservoir module formed by the two portions of FIG. 1;

FIGS. 5a-5c illustrate a mechanism holder of the reservoir module, in a longitudinal section and two views;

FIGS. 6a-6d illustrate a blocking device for a piston rod, mounted by the mechanism holder;

FIGS. 7a, 7b illustrate a piston rod in a longitudinal section and a front view;

FIGS. 8a-8c illustrates a latching block in a longitudinal section, a view and a top view;

FIG. 9 illustrates a second embodiment of an injection apparatus of the present invention;

FIG. 10 illustrates the cross-section A-A of FIG. 9;

FIG. 11 illustrates the cross-section B-B of FIG. 9;

FIG. 12 illustrates the cross-section C-C of FIG. 9;

FIG. 13 illustrates the cross-section D-D of FIG. 9;

FIG. 17 illustrates a perspective view of the dosage setting member of the second embodiment;

FIG. 18 illustrates a longitudinal view of the dosage setting member of FIG. 17;

FIG. 19 illustrates the dosage setting member of FIG. 17;

FIG. 20 illustrates a top view of the dosage setting member of FIG. 17;

DETAILED DESCRIPTION

FIGS. 1 and 2 illustrate a reservoir module 10 for use with an administering apparatus of the present invention. As shown in FIG. 1, the reservoir module 10 is formed by a reservoir part 1 and a mechanism holder 3. The reservoir part 1 and the mechanism holder 3 may be connected in any suitable manner to form the reservoir module 10. A piston rod 4 protrudes on an end of the mechanism holder 3 facing away from the reservoir part 1, into the mechanism holder 3. The piston rod 4 is mounted by the mechanism holder 3 such that it can shift in an advancing direction pointing along the longitudinal axis L of the piston rod 4, towards a front end of the reservoir part 1 facing away from the mechanism holder 3. The reservoir part 1 is substantially a hollow cylinder which has a circular cross-section and comprises a connecting region at its front end for connecting to a needle holder for an injection needle. The reservoir part 1 accommodates a reservoir container.

Figure 3:
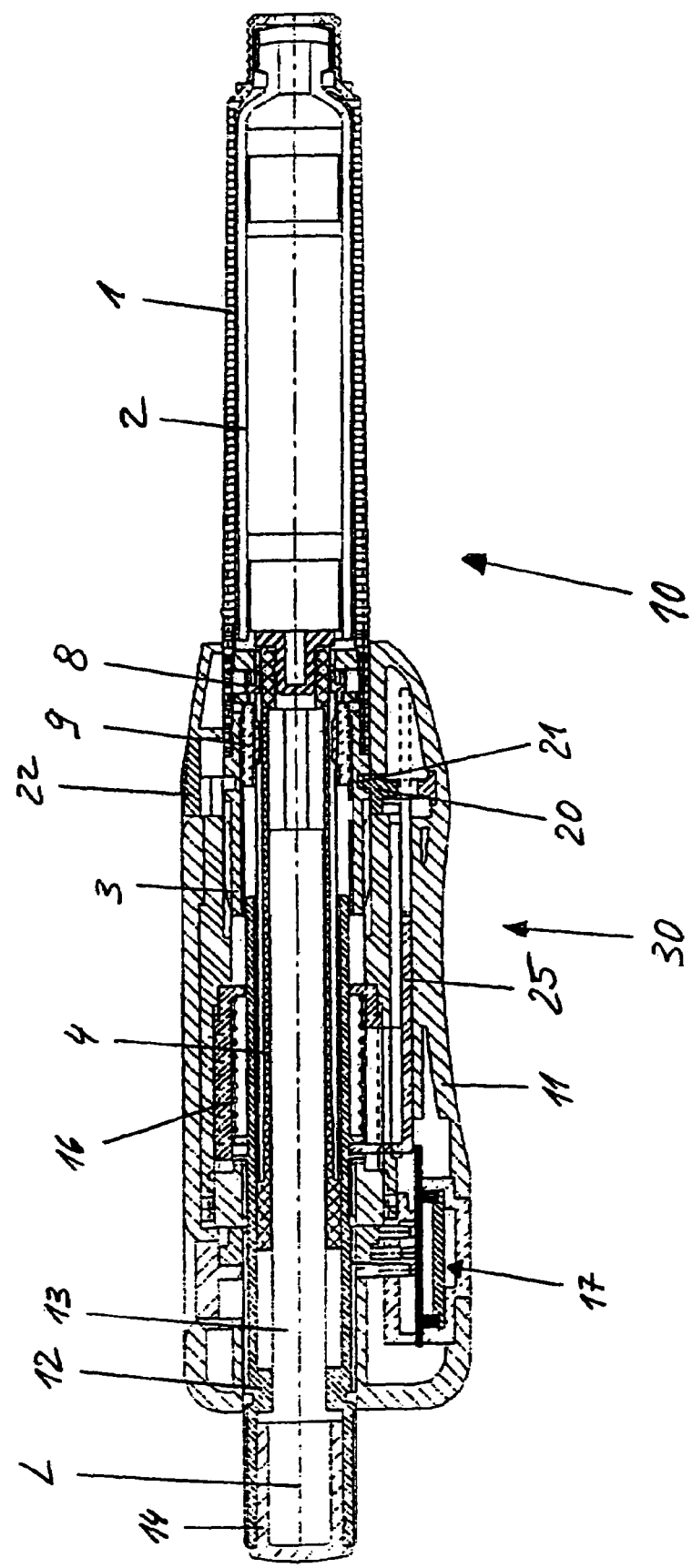
FIG. 3 illustrates a perspective view of an injection apparatus including the reservoir module of FIG. 2, in accordance with the first embodiment, in a longitudinal section.

FIG. 3 illustrates an administering apparatus with the present invention comprising an injection apparatus. As shown, the reservoir container accommodated by the reservoir part 1 is an ampoule 2. An outlet at the front end of the ampoule 2 is sealed fluid-tight by a membrane. When a needle holder is fastened to the front end of the reservoir part 1, a rear portion of the injection needle pierces the membrane, such that a fluid connection between the tip of the hollow injection needle and the reservoir 2 is established. A piston is accommodated in the ampoule 2 such that it can shift in the advancing direction towards the outlet formed at the front end of the ampoule 2. Shifting the piston in the advancing direction displaces product out of the ampoule 2 and delivers it through the outlet and the injection needle.

The piston is advanced by the piston rod 4 which pushes against the piston via its front end and thus moves the piston in the advancing direction when advanced. The piston rod 4 is held by the mechanism holder 3 such that it can be moved in the advancing direction once a certain resistance, described below, has been overcome. The mechanism holder 3 further holds the piston rod 4 such that it cannot be moved counter to the advancing direction. The piston rod 4 is prevented from moving backwards, counter to the advancing direction, by a blocking device 8. The blocking device 8 is axially fixed by the mechanism holder 3. As shown, the blocking device 8 is held in the mechanism holder 3 such that it cannot be moved in and counter to the advancing direction. The mechanism holder 3 permits the blocking device 8 to be rotated about the longitudinal axis L. The blocking device 8 also generates the resistance to be overcome to move forward.

The blocking device 8 is separately shown in FIGS. 6a-6d. The blocking device 8 is formed by an annular element which, rotatable about the longitudinal axis L, abuts the mechanism holder 3 between two facing, spaced collars 3b. The mounting of the blocking device 8 in the mechanism holder 3 can be seen in FIG. 5. The collars 3b protrude radially inwards from an inner surface of the mechanism holder 3. The collars 3b form a fixing means for axially fixing the blocking device 8.

Returning to FIG. 3, a dosage setting member 9 is accommodated in the mechanism holder 3. The dosage setting member 9, as shown, is formed as a threaded nut and is in threaded engagement with an outer thread of the piston rod 4. However, the dosage setting member 9 may be formed in any suitable manner. The dosage setting member 9 is secured against rotating by the mechanism holder 3, but is guided such that it can move axially and linearly in and counter to the advancing direction. The piston rod 4 and the dosage setting member 9 together form a spindle drive for selecting the product dosage to be administered.

The ampoule holder 1 and the mechanism holder 3 are connected to one another, secured against rotating and shifting, and together form the reservoir module 10 of the injection apparatus. The reservoir module 10 comprises the piston rod 4 held by the mechanism holder 3 with the blocking device 8, and the dosage setting member 9. The ampoule holder 1 and the mechanism holder 3 together form a front casing section of the injection apparatus. A rear casing section 11 is connected to said front casing section 1' in a positive lock. The rear casing section 11 forms the support for a dosing and activating element 12 and, together with the dosing and activating element 12 and, in some embodiments, parts of a latching means and other parts, forms a dosing and activating module 30 of the injection apparatus.

A plurality of components select the product dosage and activate the administering apparatus. These include the dosage setting member 9, the piston rod 4 and the blocking device 8. Further included is a dosing and activating device, itself comprising a plurality of components. The dosing and activating device comprises the dosing and activating element 12 and a counting and indicating means 1. The counting and indicating means 17 counts and optically indicates the selected product dosage. Of course, the dosage may be indicated by the counting and indicating means 17 in a manner other than optically, for example audibly. While the reservoir module 10 is designed as a disposable module, the dosing and activating module 30 is intended for repeated use.

Figure 4:
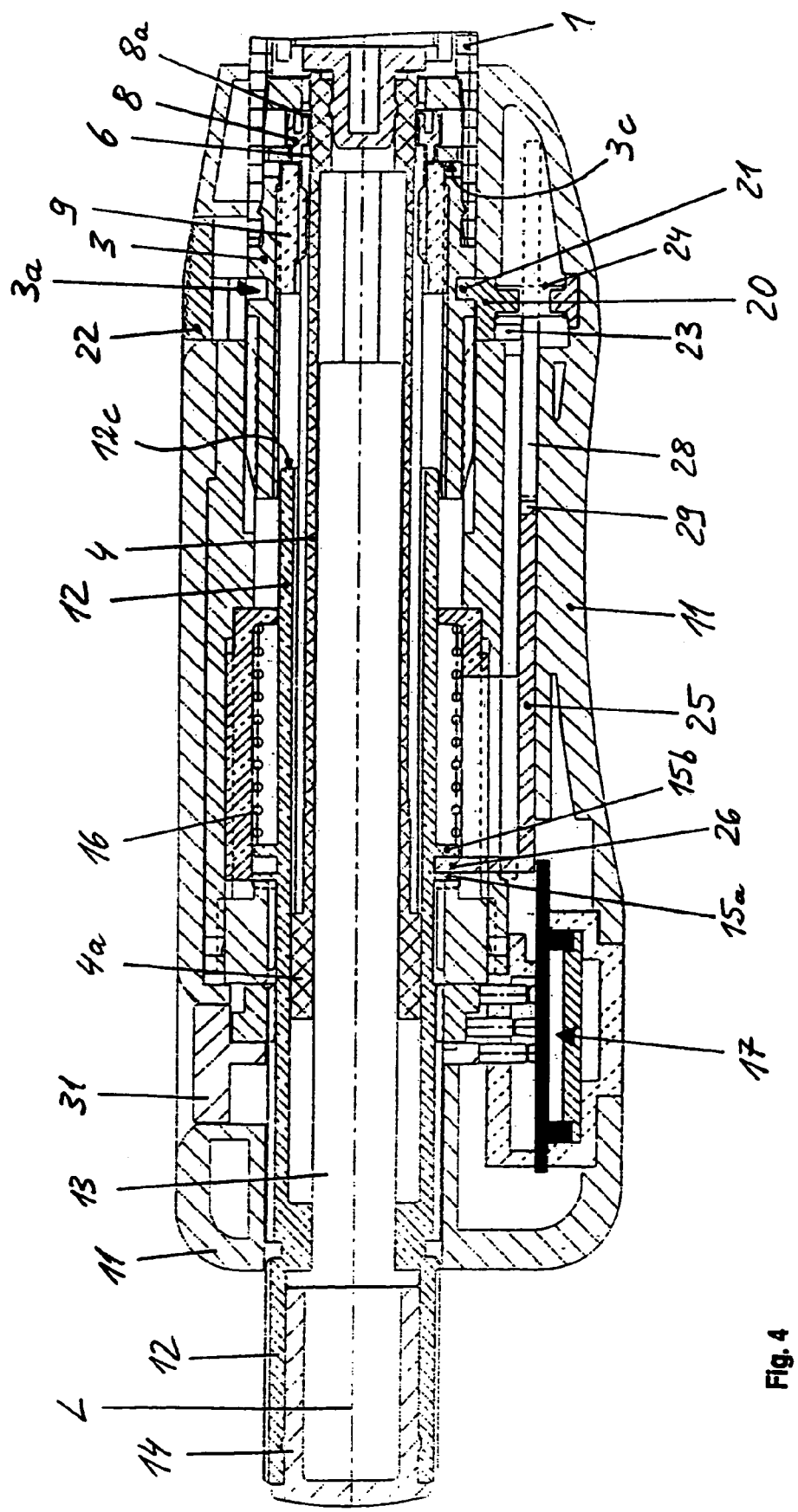
FIG. 4 illustrates a portion of the injection apparatus of FIG. 3.

For selecting the product dosage, or dosing, the dosing and activating element 12 can be rotated about the longitudinal axis L. The dosing and activating element 12 is mounted by the rear casing section 11 such that it can linearly shift along the longitudinal axis L, in and counter to the advancing direction. The dosing and activating element 12 is cylindrical and generally hollow. The dosing and activating element 12 at least partially surrounds the piston rod 4 via a front section. A rear section of the dosing and activating element 12 protrudes out beyond a rear end of the casing section 11. A rod-shaped dosing slaving means 13 is inserted into the dosing and activating element 12 from the rear, as far as a collar of the dosing and activating element 12 protruding radially inwards. At the rear end, a closure 14 is inserted into the dosing and activating element 12, approximately as far as the dosing slaving means 13. The dosing slaving means 13 is axially fixed relative to the dosing and activating element 12 between the radially protruding collar of the dosing and activating element 12 and the closure 14. The dosing slaving means 13 is also connected, secured against rotating, to the dosing and activating element 12. For dosing, the dosing slaving means 13 protrudes into the piston rod 4 from the rear. The piston rod 4 is at least partially hollow to receive the dosing slaving means 13. As shown in FIG. 4, the piston rod 4 comprises a connecting section 4a which engages with the dosing slaving means 13 such that the piston rod 4 and the dosing slaving means 13, and therefore also the dosing and activating element 12, cannot be rotated relative to one another about the common longitudinal axis L, but can be moved relative to each other along the longitudinal axis L, in and counter to the advancing direction. For this purpose, the connecting section 4*a* is formed as a linear guide for the dosing slaving means 13.

A restoring means 16 elastically tenses the dosing and activating element 12 counter to the advancing direction, into the initial position shown in FIGS. 3 and 4. In the initial position, the product can be dosed by rotating the dosing and activating element 12 about the longitudinal axis L. From the initial position, the selected product dosage can be delivered by axially shifting the dosing and activating element 12. As shown, the restoring means 16 is formed by a spiral spring acting as a pressure spring, which is accommodated in an annular gap around the dosing and activating element 12. The restoring means 16 is axially supported between a collar of the casing section 11 protruding radially inwards and a collar of the dosing and activating element 12 facing opposite and protruding radially outwards. While a spiral spring is shown, the restoring means 16 may be configured in any suitable manner.

The blocking device 8 fulfills a double function. It ensures via its blocking elements 8*a* that the piston rod 4 cannot be retracted, counter to the advancing direction, relative to the mechanism holder 3 and relative to the piston accommodated in the ampoule 2. The blocking device 8 further functions as a brake. The blocking device 8 prevents the piston rod 4 from moving forward during the dosing process in which the dosage setting member 9 is moved axially, counter to the advancing direction, towards the dosing and activating element 12.

In the initial position shown in FIGS. 3 and 4, before dosing, the dosage setting member 9 abuts against a delivery stopper 3*c*, shown in FIG. 5, formed by the mechanism holder 3, in the advancing direction. The piston rod 4 is in contract with the piston. For dosing, the dosage setting member 9 is moved away from the delivery stopper 3*c* towards the dosing and activating element 12 by the threaded engagement with the piston rod 4 and the linear guide from the mechanism holder 3. This reduces a slight distance between a rear stopper area of the dosage setting member 9 and a front stopper area of the dosing and activating element 12, but increases a slight distance between a front stopper area of the dosage setting member 9 and the delivery stopper 3*c*. The distance between the dosage setting member 9 and the delivery stopper 3*c* is the path length by which the dosage setting member 9 and, due to the threaded engagement, the piston rod 4 are moved in the advancing direction during the delivery movement of the dosing and activating element 12. The delivery stopper 3*c* forms a front translational stopper. During the delivery movement, the piston rod 4 pushes via its front end, which is formed by a plunger body connected to the piston rod 4 such that it cannot move in or counter to the advancing direction, against the piston and pushes the piston forwards in the advancing direction towards the outlet of the ampoule 2. The longitudinal axis L forms the rotational and translational axis of the movements which are performed to dose and deliver the product.

The distance between the dosage setting member 9 and the dosing and activating element 12 during the dosing process when the dosage setting member 9 abuts against the delivery stopper 3*c* corresponds to the maximum product dosage which can be selected and delivered. The stroke movement of the dosing and activating element 12 is of equal length for each delivery. Dosing merely sets the distance between the dosage setting member 9 and the delivery stopper 3*c* and, thus, the path length which can be jointly traveled by the dosing and activating element 12 and the dosage setting member 9 during delivery. The dosing and activating element 12 forms a rear translational stopper 12*c* which limits the translational dosing movement of the dosage setting member 9 and thus defines the maximum delivery stroke which may be set.

The blocking device has a braking function and, therefore, a braking engagement exists between the piston rod 4 and the blocking device 8. FIGS. 6*a* through 6*d* and FIGS. 7*a* and 7*b* illustrate the blocking device 8 and its engagement with the piston rod 4. The blocking device 8 comprises two braking elements 8*b* for the braking engagement, which, as shown, are each formed by an elastically flexing catch, like the blocking elements 8*a* before them. In the embodiment shown, the blocking device 8 is formed by an annular element from which four elastic catches axially project on an abutting side. The catches are arranged in a uniform distribution over the circumference of the annular element. Two mutually opposing catches form the blocking elements 8*a* and the other two catches, likewise arranged mutually opposing, form the braking elements 8*b*. Alternately, the blocking device 8 may be formed in any suitable configuration. Likewise, if provided, each of the blocking elements 8*a* and braking elements 8*b* may be formed in any suitable manner.

The piston rod 4 accordingly includes two returning blocking means 6, which are formed on opposing sides on the outer surface of the piston rod 4 and extend in the longitudinal direction. The piston rod 4 further includes two advancing braking means 7, which likewise extend in the longitudinal direction of the piston rod 4 on mutually opposing sides. The thread of the piston rod 4 for threaded engagement of the piston rod 4 with the dosage setting member 9 is formed by four remaining threaded sections 5 which extend over almost the entire length of the piston rod 4. The returning blocking means 6 and the advancing braking means 7 are each formed by a row of teeth. However, while the teeth of the returning blocking means 6 are formed as serrated teeth, narrowing in the advancing direction and comprising blocking areas pointing backwards and extending transverse to the advancing direction, the rows of teeth which form the advancing braking means 7 do not comprise blocking areas pointing forwards having a comparable blocking effect. The teeth of the advancing braking means 7 each exhibit a softer tooth profile as compared to the returning blocking means 6. Of course, the returning blocking means 6 and the advancing braking means 7 may alternately be formed in any suitable manner. The braking engagement between the blocking device 8 and the advancing braking means 7 of the piston rod 4 is not intended to prevent the piston rod 4 from being advanced, but merely to make it more difficult, thereby ensuring that the piston rod 4 is not moved in the advancing direction during dosing. The front sides of the teeth of the advancing braking means 7 and the rear sides of the braking elements 8*b*, which contact the front sides of the teeth of the advancing braking means 7, are configured such that a threshold force which is not reached during dosing has to be exceeded to overcome the braking engagement. This threshold force exceeds the force required to move the teeth of the returning blocking means 6 over the blocking elements 8*a* in the advancing direction. The threshold force is preferably at least twice as large as the initial frictional force between the returning blocking means 6 and the blocking elements 8*a*.

The frictional force between the latter increases gradually between two consecutive blocking engagements during the advancing movement. The threshold force of the braking engagement, by contrast, has to be applied from one blocking engagement to the next, immediately at the beginning of the advancing movement, in each blocking engagement. Regardless, the threshold force should not, be so large as to distract the user during delivery.

An undesired advancing movement by the piston rod responsive to the movement by the dosage setting member 9 when selecting the dosage may be prevented by the blocking engagement of the blocking device 8 alone. However, such a movement is more reliably prevented in conjunction with the braking engagement than by relying the blocking engagement alone.

The connection between the reservoir module 10 and the dosing and activating module 30 is a positive lock. A latching engagement exists between the mechanism holder 3 and the casing section 11 which prevents relative movement in the axial direction. Beyond the latching engagement, the front casing section 1' and the rear casing section 11 are guided axially and linearly directly onto one another to prevent relative rotating when connected. The axial guides 3d of the mechanism holder 3, which together with one or more corresponding engagement elements of the rear casing section 11 form the linear guide, can be seen in FIGS. 5a-5c. As shown, the axial guides 3d are formed by guide areas on guide ribs. The axial guides 3d may alternately be formed by guide areas in axially extending recesses, thus forming axial guide channels. The guide ribs are axially tapered, such that insertion funnels leading into the guide channels are formed for the one or more engagement elements of the rear casing section 11. To better center the casing sections 1' and 11 at the beginning of connecting, the guide ribs are also tapered in the radial direction. The one or more engagement elements of the rear casing section 11 may be formed like the axial guides 3d on the inner surface area of the rear casing section 11.

A latching engagement exists between a first, female latching element 3a of the mechanism holder 3 and a latching ring 20 which is connected to the rear casing section 11 such that it can move radially but not axially. The latching ring 20 forms a second, male latching element 21 which radially engages directly with the first latching element 3a. A lock/latch connection exists between the first latching element 3a and the second latching element 21 which prevents the reservoir module 10 and the dosing and activating module 30 from moving axially relative to one another.

Returning to FIGS. 3 and 4, the second latching element 21 in latching engagement with the first latching element 3a. The first latching element 3a is formed by an annular stay and a groove which runs around the outer surface of the mechanism holder 3. The annular stay forms a rear side wall of the groove. The second latching element 21 is formed by a cam which protrudes radially inwards from the inner surface of the latching ring 20 and which in the latching engagement is pushed radially inwards over an inner surface area of the rear casing section 11, protruding into the accommodating latching element 3a, by a restoring means 24. The latching ring 20 is supported in the radial direction on an inner surface area formed by the rear casing section 11, by the restoring means 24, such that the restoring means 24 pushes against the outer surface of the latching ring 20 roughly in a radial extension of the latching element 21. The latching ring 20 surrounds the mechanism holder 3 and can be moved radially back and forth against the restoring force of the restoring means 24, such that the second latching element 21 can be moved in and out of latching engagement with the first latching element 3a. The rear casing section 11 forms a tight sliding guide for the radial movement of the latching ring 20. On its side radially opposite the latching element 21, the latching ring 20 forms an unlatching button 22. To radially guide the restoring means 24, formed as a pressure spring, a guide cam projects radially from the outer surface area of the latching ring 20 facing away from the latching element 21.

Two blocking cams 23 are provided to prevent a radial movement of the second latching element 21. Such radial movement could otherwise result in the latching engagement being released. The blocking cams 23 press radially outwards against a latching block 25 and project from the outer surface area of the latching ring 20, in the circumferential direction on both sides of said guide cam and axially behind the guide cam. The blocking cams 23 thus abut against the latching block 25. The latching engagement between the latching elements 3a and 21 is thus secured by the latching block 25. The latching engagement is secured in each position of the dosing and activating element 12, except for a releasing position which the dosing and activating element 12 assumes at the end of its delivery movement. The releasing position coincides with the foremost shifting position of the dosing and activating element 12 when it abuts the dosage setting member 9 during its delivery movement and the dosage setting member 9 abuts against the delivery stopper 3c of the mechanism holder 3. Providing the dosing and activating module 30 is not yet connected to the reservoir module, a mechanical stopper for the dosing and activating element 12 is formed by a stopper element 31 of the dosing and activating device. In the embodiment shown, a reset holder ring which resets the indicator 17 forms the stopper element 31. The dosing and activating element 12 abutting against the stopper element 31 defines the releasing position of the dosing and activating element 12. The releasing position defined by the stopper element 31 corresponds to that defined by the dosage setting member 9 abutting the delivery stopper 3c.

FIGS. 8a through 8c illustrate the latching block 25. As shown, the latching block 25 is formed by a blocking slider as a unitary piece. The latching block 25 comprises a plate-shaped main body which extends axially when assembled, as for example shown in FIG. 4. At one end, a stay 26 projects at approximately right angles from the main body. When assembled, the stay 26 extends radially approximately as far as the dosing and activating element 12. The stay 26 fastens the latching block 25 to the dosing and activating element 12 which, for this purpose, comprises two annular stays formed axially spaced on an outer surface area. The two annular stays form the slaving means 15a and 15b. The front slaving means 15a also forms the support collar for the restoring means 16. The latching block 25 is tightly enclosed axially on both sides by the two slaving means 15a and 15b. The latching block 25 protrudes into the annular space formed between the two slaving means 15a and 15b via its stay 26.

At a front end facing away from the stay 26, the main body of the latching block 25 is provided with an axial recess 27 which is open towards the front end of the latching block 25. Blocking tongues 28 extending axially on both sides of the recess 27 are thus formed. The blocking cams 23 of the latching ring 20 are arranged such that each of the blocking cams 23 pushes against one of the blocking tongues 28, providing the dosing and activating element 12 does not assume the releasing position. When the latching block 25 moves axially, the restoring means 24 for the latching element 21 extends through the axial recess 27. Indentation recesses 29 are furthermore formed in the main body of the latching block 25, and define the releasing position of the dosing and activating element 12. One indentation recess 29 is provided for each of the blocking cams 23. The position of the indentation recesses 29 is selected such that they only overlap the blocking cams 23, and thus allow the blocking cams 23 to be inserted, when the dosing and activating element 12 has been advanced into its releasing position.

Of course, in the arrangement shown, a single blocking cam 23 could also be provided and the latching block 25 accordingly comprise only one indentation recess 29 and as well as only one blocking tongue 28. The latching block 25 may alternately be produced together with the dosing and activating element 12 as a unitary piece. Further, any other suitable configuration for the latching block 25 may be used. With respect to the installation length of the latching block 25, the latching block 25 is supported, on its outer side facing away from the latching element 21, on an inner surface area of the casing 11. This increases the stability of securing the latching engagement. The casing 11 preferably forms an axial guide for the latching block 25.

The functionality of the injection apparatus is described in the following, wherein it is assumed that a new reservoir module 10 and a dosing and activating module 30 which has already been used at least once are assembled and a product is then delivered for the first time.

The dosing and activating module 30 and the new reservoir module 10 are aligned axially with respect to one another, such that their two longitudinal axes are flush with one another. The reservoir module 10 is inserted via its rear end into the casing 11, which is open to the front, of the dosing and activating module 30. This centers the casing section 1' and the casing section 11 on the tapered ends of the guide ribs 3d of the mechanism holder 3. The two casing sections are guided axially and linearly onto one another in a rotational angular position pre-set by the linear guide, until the casing sections 1' and 11 assume a connecting end position in which the latching engagement of the latching elements 3a and 21 can be established.

The dosing and activating element 12 is locked in pre-set rotational angular positions relative to the rear casing section 11. The linear guide of the casing sections 1' and 11 and the rotational angular locking positions of the dosing and activating element 12 are adjusted to one another such that the engagement, secured against rotating, between the dosing and activating element 12 and the piston rod 4 is established in each locking position of the dosing and activating element 12 and each rotational angular position in which the casing sections 1' and 11 are linearly guided onto one another.

If the dosing and activating element 12 is situated in an axial position relative to the casing section 11 which is behind the releasing position, the latching element 21 is held in its radially innermost position by the latching block 25. In this position of the latching element 21, the dosing and activating module 30 and the reservoir module 10 cannot be slid onto each other up to the connecting end position and therefore also cannot be connected to one another, as the annular stay formed on the outer surface of the mechanism holder 3, which forms a part of the first latching element 3a, comes to rest abutting against the second latching element 21 first.

The annular stay may be reduced to a short radial protrusion in the tangential direction, if it is ensured that the casing sections 1' and 11 can only be assembled in the rotational angular position in which such a protrusion and the second latching element 21 come to rest in an axial flush. The annular stay or radial protrusion may also form the first latching element 3a. The first latching element 3a allows the connection between the reservoir module 10 and the dosing and activating module 30 to be established only when the dosing and activating element 12 assumes its releasing position. If this condition is fulfilled, the dosing and activating element 12 ensures, when the connection between the reservoir module 10 and the dosing and activating module 30 is established, that the dosage setting member 9 is situated in its dosing zero position, abutting the delivery stopper 3c of the mechanism holder 3.

To fulfill the above-described condition, wherein the dosing and activating element 12 assumes its released position, the user pushes the dosing and activating element 12 axially forwards relative to the rear casing section 11 approximately as far as the releasing position. In this relative position between the rear casing section 11 and the dosing and activating element 12, the blocking cams 23 may be moved into the indentation recesses 29 of the latching block 25. The user therefore not only pushes the dosing and activating element 12 but also pushes the second latching element 21 out of latching engagement by using the unlatching button 22. The reservoir module 10 may then be moved axially over the annular stay of the first latching element 3a and inserted further into the rear casing section 11. The user can release the unlatching button 22. When the second latching element 21 overlaps the first latching element 3a, the second latching element 21 snaps into the accommodating first latching element 3a due to the force of the restoring means 24, such that the latching engagement is established. The reservoir module 10 and the dosing and activating module 30 are then connected to each other in a defined way with respect to the position of the dosage setting member 9 and the piston rod 4. If the dosage setting member 9 still exhibited a slight distance from the delivery stopper 3c before the latching engagement is established, this distance is generally eliminated by the action of the dosing and activating element 12 required to establish the connection. A resultant delivery of product can be accepted for priming the injection needle. This preferably resets the counting and indicating means 17 to zero.

In the defined initial, the user can dose the product. The product is dosed by rotating the dosing and activating element 12 about the longitudinal axis L and relative to the casing section 11. As the dosing slaving means 13 is connected to the dosing and activating element 12, secured against rotating, and engages with the piston rod 4, secured against rotating, the dosing and activating element 12 slaves the piston rod 4 during its rotational dosing movement. Due to the threaded engagement between the piston rod 4 and the dosage setting member 9 and the linear guide of the dosage setting member 9 by the mechanism holder 3, the dosage setting member 9 performs an axial, translational dosing movement, pre-set by the thread pitch of the reciprocal threaded engagement, towards the dosing and activating element 12. The rear translational stopper 12c formed by the dosing and activating element 12 limits the translational dosing movement of the dosage setting member 9 and defines the maximum delivery stroke which may be set.

The counting and indicating means 17 counts the dosage units corresponding to the rotational angular position of the dosing and activating element 12 and indicates it optically.

Once the desired product dosage has been selected, the dosing process is completed. The selected product dosage is delivered by the delivery movement, pointing in the advancing direction of the piston, of the dosing and activating element 12. During the delivery movement, the dosing and activating element 12 abuts against the dosage setting member 9 and slaves it. When the dosage setting member 9 abuts against the delivery stopper 3*c* of the mechanism holder 3 during the delivery movement, the delivery movements of the dosing and activating element 12 and the delivery of product are completed. Once the user releases the dosing and activating element 12, the dosing and activating element 12 is moved counter to the advancing direction and returned to a new initial position for dosing and delivering the product again, by the restoring means 16. The counting and indicating means 17 is preferably coupled to the dosing and activating element 12 such that it resets to zero after delivery of the product. Further, the counting and indicating means 17 may be configured such that it counts and indicates the total product amount already delivered and thus the residue product amount remaining in the ampoule 2.

To detach the reservoir module 10 from the dosing and activating module 30, the dosing and activating element 12 is advanced to the releasing position, i.e. until it abuts against the dosage setting member 9. The user releases the latching engagement by pushing the unlatching button 22 and separates the reservoir module 10 from the dosing and activating module 30.

FIGS. 9 to 13 illustrate a second embodiment of an injection apparatus in accordance with an administering apparatus of the present invention. The injection apparatus of the second embodiment corresponds with that of the first embodiment with respect to the latch and latching block 25, such that reference is made in this regard to the description of the first embodiment. The latching block 25 of the second embodiment reflects that of the first embodiment with respect to all its functional details. The same applies to the latching elements 3*a* and 21.

The latching ring 20 and the position of the blocking cams 23 relative to the latching element 21 and relative to the latching block 25 in the initial state of the apparatus is shown in the cross-sections of FIGS. 10, 11 and 12, to which reference is made in this regard, also as representative for the first embodiment.

The injection apparatus of the second embodiment differs from the first embodiment in the engagement and the progression of movement of the components involved in dosing. Furthermore, the mechanism holder, in addition to the functions of the mechanism holder of the first embodiment, positions the dosage setting member in discrete rotational angular positions which may be changed relative to the mechanism holder, for the purpose of dosing. The blocking means of the second embodiment, by contrast, is embodied more simply than that of the first embodiment. For the most part, the differences as compared to the first embodiment will be described in the following, wherein for components which are identical in their basic function to the components of the same name in the first embodiment but differ in details, numbers in the thirties with the same end digit, or exactly the same reference numerals as in the first embodiment, are used. Where no statements are made regarding the second embodiment, the corresponding statements regarding the first embodiment shall apply.

In the second embodiment, the dosing and activating element 32, which can be moved axially and linearly relative to the rear casing section 11 and rotated about the longitudinal axis L, is connected to the dosage setting member 39, secured against rotating. The dosing and activating element 32 and the dosage setting member 39 can be moved in and counter to the advancing direction, relative to one another and relative to casing sections 1' and 11. The piston rod 4 is held by a mechanism holder 3, secured against rotating. In cooperation with blocking elements of the blocking device 38, formed on the mechanism holder 3 as a unitary piece, the returning blocking means 6, which is functionally identical to the first embodiment, prevents the piston rod 4 from moving counter to the advancing direction, but allows it to move in the advancing direction. The blocking elements forms both the returning block and the rotational block for the piston rod 4. Furthermore, as previously in the first embodiment, the dosing and activating element 32 forms a sliding guide for the piston rod 4.

During dosing, the dosing and activating element 32 performs the same rotational dosing movement as the dosing and activating element 12 of the first embodiment. However, as the engagement is secured against rotating, the dosage setting member 39 is slaved during the rotational dosing movement. The threaded engagement between the piston rod 4 and the dosage setting member 39 is again comparable to that of the first embodiment. Due to the rotational dosing movement and the threaded engagement with the piston rod 4, a stopper 39*c* formed by the dosage setting member 39 is moved, during dosing, counter to the advancing direction, towards a front end of the dosing and activating element 32. As opposed to the first embodiment, the dosage setting member 39 thus completes a rotational dosing movement and a translational dosing movement relative to the front casing section during dosing, while the piston rod 4 remains stationary. Once dosing has been completed, the delivery movement of the dosing and activating element 32 advances the piston rod 4 by the path length which corresponds to the slight distance between a stopper area of the dosage setting member 39 and the delivery stopper 3*c* of the mechanism holder 3, set by the dosing.

The translational dosing movement of the dosage setting member 39 is limited counter to the advancing direction by a rear translational stopper 11*c* which is formed directly by the rear casing section 11. The rotational and translational axis of the components involved in dosing and delivering the product forms the longitudinal axis L.

As in the first embodiment, the front casing section 1' forms a sliding guide for the dosage setting member 39. In order to form the sliding guide, an inner surface area of the mechanism holder 3 and an outer surface area of the dosage setting member 39 are in sliding contact with each other. The dosing and activating element 32 engages with an inner surface area of the dosage setting member 39, to form the connection, secured against rotating, between the dosage setting member 39 and the dosing and activating element 32.

In the second embodiment, the piston rod 4 comprises no braking means of its own beyond the returning blocking means 6. Rather, the front sides of the serrated teeth of the returning blocking means 6 also form the braking means. The piston rod 4 of the second embodiment can, however, be replaced by the piston rod 4 of the first embodiment. Accordingly, the mechanism holder 3 of the second embodiment may form at least one braking element, and preferably both braking elements, of the first embodiment.

Figure 14:
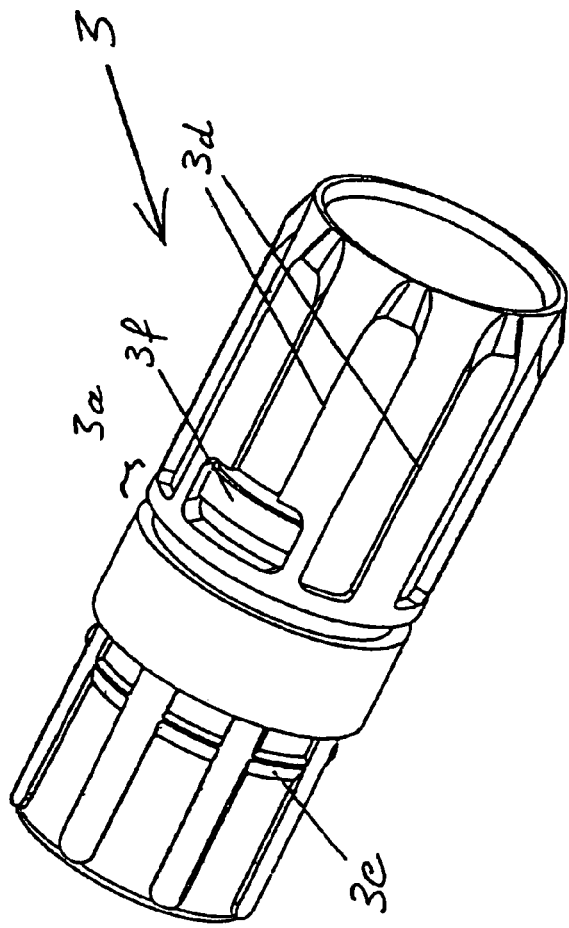
FIG. 14 illustrates a perspective view of the mechanism holder of the second embodiment of the present invention.
Figure 15:
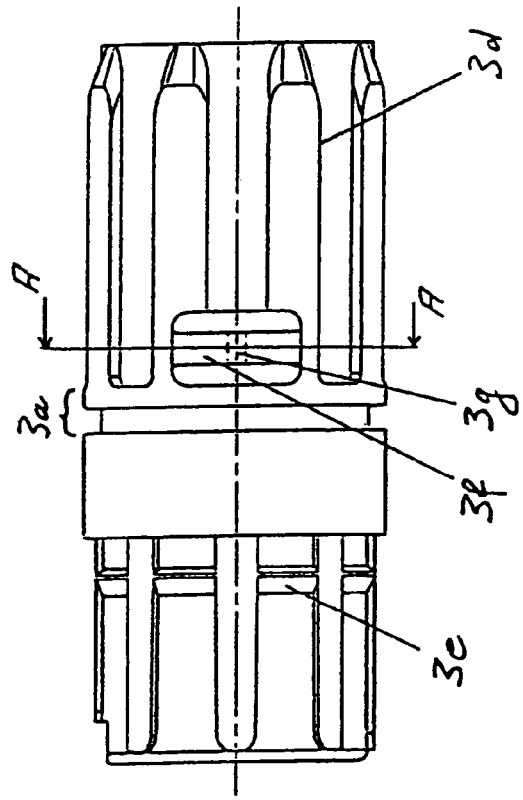
FIG. 15 illustrates the mechanism holder of FIG. 14, in a view.
Figure 16:
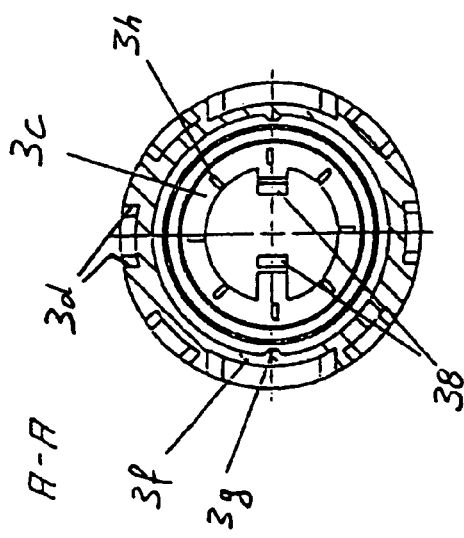
FIG. 16 illustrates the cross-section A-A of FIG. 15.

FIGS. 14 to 16 illustrate the mechanism holder 3 of the second embodiment in a perspective representation, a side view and in the cross-section A-A indicated in the side view. As in the first embodiment, the mechanism holder 3 is embodied as a unitary sleeve part, for example as a plastic injection molded part. It comprises a bulge 3*e* on the outer surface of a front sleeve section. The front sleeve section is plugged into the reservoir part 1 and locked non-detachably, at least for the user, to the reservoir part 1 by the bulge 3*e*.

The latching element 3a is formed on a middle sleeve section of the mechanism holder 3, as in the first embodiment. A rear sleeve section, connected to the latching element 3a, forms a plurality of axial guides 3d on its outer circumference. The axial guides 3d are formed by guide ribs which protrude radially on the outer circumference of the rear sleeve section. The axial guides are formed by the axially extending, straight side walls of said guide ribs, such that, as in the first embodiment, axial guiding channels are obtained. The guide ribs protrude from the middle sleeve section, approximately as far as the rear end of the mechanism holder 3, where they taper axially. The axial guide 3d linearly guides the rear casing section 11 when the reservoir module 10 is connected to the dosing and activating module 30. As can be seen in FIGS. 9 and 11, engagement elements 11d project radially inwards from the inner surface area of the rear casing section 11. One engagement element 11d protrudes into each of the axial guides 3d and is linearly guided by the axial guide 3d when the front casing section 1' and the rear casing section 11 are slid into one another. This restricts relative rotating between the front casing section 1' and the rear casing section 11 during engagement, secured against rotating, between the dosing and activating element 32 and the dosage setting member 39.

As the guide ribs taper axially at their rear ends, and the guide channels are thus widened into insertion funnels, centering between the front casing section 1' and the rear casing section 11, for the purpose of connecting, is simplified. The guide ribs also taper at their ends radially with respect to the surface area of the mechanism holder 3, which simplifies centering the casing sections 1' and 11 into a rotational angular position pre-set by the axial guide 3d, relative to one another.

Just as the front casing section 1' and the rear casing section 11 are prevented from rotating relative to one another during connection, the dosage setting member 39 is also fixed with respect to its rotational angular position relative to the front casing section 1'. The dosage setting member 39 is detachably fixed to allow the rotational movement of the dosage setting member 39 necessary for dosing. To enable the dosing movement of the dosage setting member 39 but prevent an undesired dosing movement by establishing the connection between the front casing section 1' and the rear casing section 11, the dosage setting member 39 is fixed by the mechanism holder 3 in discrete rotational angular positions, by a releasable locking connection.

FIGS. 17 to 20 show individual representations of the dosage setting member 39. For forming the locking connection, a number of locking recesses 39g are formed on the outer surface area of the dosage setting member 39, distributed in generally regular intervals over the circumference of the dosage setting member 39. Each of the locking recesses 39g is formed by a straight, axially extending furrow having a rounded contour running in its cross-section. Of course, the locking recesses 39g may alternately be formed in any suitable manner.

Returning to FIGS. 15 and 16, the mechanism holder 3 is provided with two locking projections 3g. The two locking projections 3g project radially inwards from an inner surface area of the mechanism holder 3 in the rear sleeve section of the mechanism holder 3. The two locking projections 3g, as shown, are arranged diametrically opposed to one another. The respective surface region of the mechanism holder 3, on which one of the locking projections 3g is formed, forms a spring element 3f which is elastically flexible in the radially direction. Due to the elastic flexibility and the rounded shape of the locking projections 3g, in conjunction with the rounded profile of the locking recesses 39g, the locking engagement between the locking projections 3g and the opposing locking recesses 39g may be released. Releasing the locking engagement between the locking projections 3g and the opposing locking recesses 30g allows the dosage to be selected. The locking engagement is designed, however, such that the dosage setting member 39 is rotationally angularly fixed and undesired dosing movement of the dosage setting member 39 is prevented when the front casing section 1' and the rear casing section 11 are connected and when the rotational coupling between the dosing and activating element 32 and the dosage setting member 39 is established. The locking connection between the mechanism holder 3 and the dosage setting member 39 has the advantageous side effect of a tactile signal during dosing. To maintain the elasticity of the spring element 3f, the rear sleeve section of the mechanism holder 3 is cut away in the surface region, such that the spring element 3f is maintained as an annular segment extending in the circumferential direction which is axially free on both sides.

Returning to FIGS. 17 through 20, axial guides 39d are provided for the engagement, secured against rotating, between the dosage setting member 39 and the dosing and activating element 32. The dosing and activating element 32 is provided with at least one engagement element, in order to obtain the axial linear guide, i.e. the rotational block, between the dosing and activating element 32 and the dosage setting member 39. The axial guides 39d are again guide channels formed by a number of guide ribs extending axially in a straight line. Each of the guide ribs tapers axially and radially at its rear end facing the dosing and activating element 32, thus simplifying centering between the dosing and activating element 32 and the dosage setting member 39, when the engagement, secured against rotating, is established. The same design is therefore used for the axial linear guide of the dosage setting member 39 and the dosing and activating element 32 as for the axial linear guide of the casing sections 1' and 11.

Figure 22:
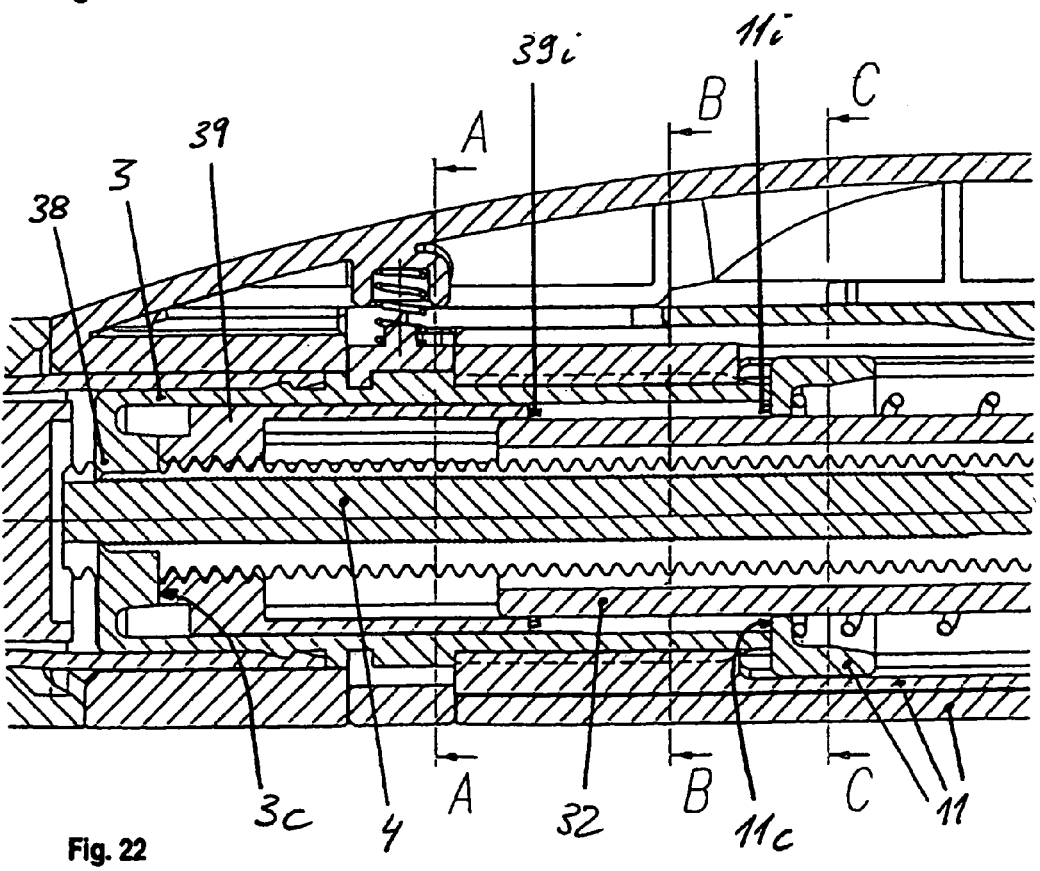
FIG. 22 illustrates a portion of the injection apparatus in accordance with FIG. 9.

The dosing setting member 39 is further provided with a dosing thread 39a and a delivery stopper 39c. Two rotational blocks are provided for the dosage setting member 39 which are active in the two axial end positions of the dosage setting member 39. Reference is additionally made in this regard to FIG. 22.

To prevent retraction of the piston rod 4 in response to a rotational dosing movement by the dosage setting member 39, rotational stoppers 39h are formed at a front end of the dosage setting member 39. In the front position, which the dosage setting member 39 assumes directly after the product is delivered or before the dosage is selected, the rotational stoppers 39h engage with rotational counter stoppers 3h formed on the mechanism holder 3 (FIG. 16). The rotational stoppers 39h axially project from a front abutting side of the dosage setting member 39, and the rotational counter stoppers 3h protrude from an axially facing abutting area of the mechanism holder 3 forming the delivery stopper 3c, axially opposed to the rotational stoppers 39h. The engagement between the rotational stoppers 39h and the rotational counter stoppers 3h is such that it allows a rotational dosing movement in a rotational direction, which causes a translational dosing movement of the dosage setting member 39 directed away from the delivery stopper 3c, but prevents a rotational dosing movement in the opposite rotational direction, in the front axial end position.

A further pair of rotational stoppers and rotational counter stoppers is provided, which are formed and cooperate in basically the same way as the stoppers 3h and 39h. The second pair of rotational stoppers are rotational stoppers 39i which axially project from a rear abutting area of the dosage setting member 39, and rotational counter stoppers 11i which axially protrude from the facing stopper abutting area of the rear translational stopper 11c towards the dosage setting member 39. The rotational counter stoppers 11i cannot be seen in FIG. 9 due to their small dimensions. In the rear end position, the rear pair of rotational stoppers 11i/39i prevents the the piston rod 4 from being moved in the advancing direction in response to a dosing movement by the dosage setting member 39, directed against the rear translational stopper 11c.

The height, or axial length, of all the rotational stoppers 3h, 39h, 11i and 39i is adjusted to the thread pitch of the engaged dosing thread of the piston rod 4 and the dosage setting member 39. The rotational stoppers are axially sufficiently short that the rotational dosing movement which moves the dosage setting member 39 away from the respective translational stopper 3c or 11c is not impeded.

When assembling the components of the reservoir module 10, the dosage setting member 39 is screwed onto the piston rod 4 as far as a pre-set axial position, as may be seen from FIG. 9. The piston rod 4, together with the screwed-on dosage setting member 39, is then inserted into the mechanism holder 3 from behind, until its blocking device 38 comes into blocking engagement with the returning blocking means 6 of the piston rod 4 and the engagement, secured against rotating, between the rotational stoppers 39h of the dosage setting member 39 and rotational counter stoppers of the mechanism holder 3 is established. During insertion into the mechanism holder 3, the dosage setting member 39 is axially and linearly guided by the mechanism holder 3 via the locking engagement between the locking projections 3g and the locking recesses 39g, until the dosage setting member 39 abuts the delivery stopper 3c of the mechanism holder 3. In this front end position of the dosage setting member 39 relative to the mechanism holder 3, the engagement, secured against rotating, between the rotational stoppers 3h and 39h is established. In this state, the mechanism holder 3 and a reservoir part 1, already fitted with a reservoir, are connected to each other.

In a following step, the rear casing section 11 of the assembled dosing and activating module 30 is slid onto the mechanism holder 3, wherein the mechanism holder 3 and the rear casing section 11 can be centered with respect to each other due to the axial guides 3d and the engagement elements 11d of the rear casing section 11. Once centered, the mechanism holder 3 and the rear casing section 11 are axially and linearly guided onto one another due to the guide engagement. In the course of sliding the rear casing section 11 onto the mechanism holder 3, the dosing and activating element 32 comes into engagement, secured against rotating, with the dosage setting member 39, wherein centering is also possible, using a linear guide corresponding to the axial guides 3d and the engagement elements 11d.

The dosing and activating element 32 is in locking engagement with the rear casing section in discrete rotational angular locking positions and in the locking engagement, i.e. in the respective rotational angular locking position, is axially and linearly guided. The rotational angular difference between two consecutive rotational angular locking positions corresponds to one dosage unit. The linear guide between the mechanism holder 3 and the rear casing section 11 and the discrete rotational angular positions of the dosage setting member 39 relative to the mechanism holder 3 (locking projections 3g and locking recesses 39g) and the rotational angular locking positions of the dosing and acti-vating element 32 relative to the rear casing section 11 are adjusted to one another such that the two casing sections 1' and 11 are-slid linearly over one another in a rotational angular position. Thus, the dosage setting member 39 and the dosing and activating element 32 are also aligned relative to one another for their engagement, secured against rotating, such that there is no relative rotating between the components involved in dosing while the reservoir module 10 is connected to the dosing and activating module 30.

With respect to the other details of assembling, in particular of establishing the latching engagement, and of the functionality of the injection apparatus in accordance with the second embodiment, reference is made to the description of first embodiment.

Figure 21:
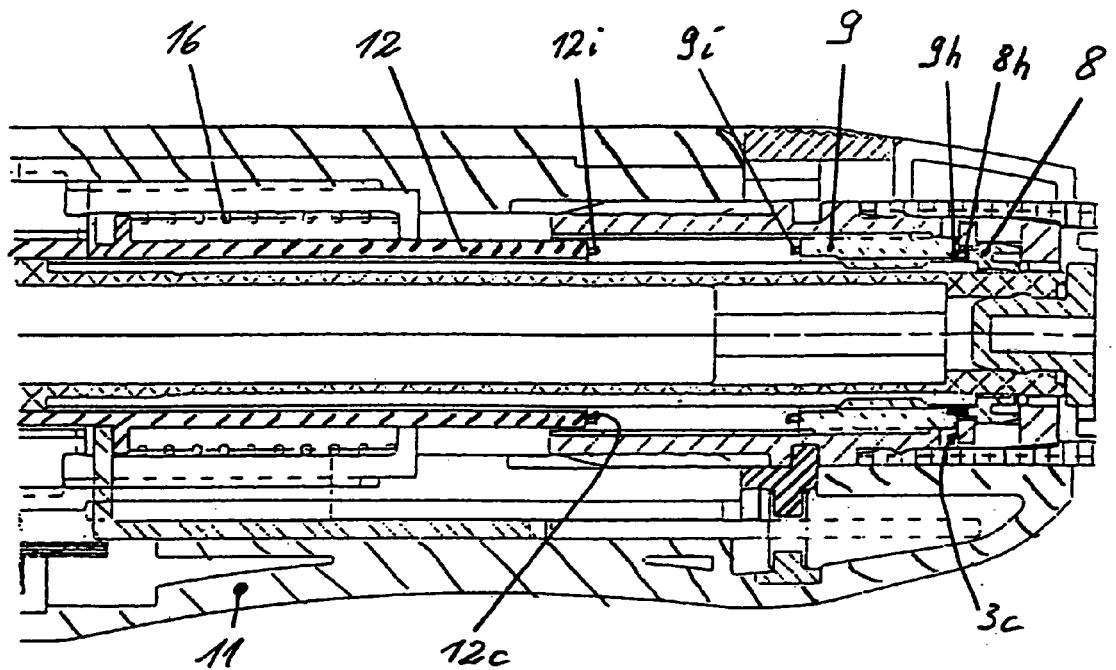
FIG. 21 illustrates a portion of the injection apparatus in accordance with FIG. 3.

As shown in FIG. 21, rotational blocks may also be provided in the injection apparatus of the first embodiment. The rotational blocks prevent undesired response movements by the piston rod 4 in the two axial end positions of the dosage setting member 9 of the first embodiment. The two rotational blocks are formed in the same way as the rotational blocks of the second embodiment. However, the rotational counter stoppers which in the second embodiment are formed on the casing sections 1' and 11 are formed in the first embodiment by the blocking device 8 and the dosing and activating element 12. Thus, a number of rotational stoppers 8h are formed on the abutting side of the blocking device 8 axially facing the dosage setting member 9 and axially protrude towards the dosage setting member 9. As the blocking device 8 is axially and immovably mounted by the front casing section 1' and connected, secured against rotating, to the piston rod 4, a rotational block for the rotational dosing movement between the piston rod 4 and the dosage setting member 9 is also obtained, via the front pair of rotational stoppers 8h/9h. A second pair of rotational stoppers is formed between the dosage setting member 9 and the rear translational stopper 12c. As in the second embodiment, a number of rotational stoppers 12i protrude axially towards the dosage setting member 9 from the abutting area of the translational stopper 12c axially facing the dosage setting member 9. As in the second embodiment, the dosage setting member 9 is provided on its rear side with rotational stoppers 9i which, in the rear axial end position of the dosage setting member 9, engage with the rotational stoppers 12i. In the rear axial end position of the dosage setting member 9, the rear pair of rotational stoppers 9i/12i only allows the rotational dosing movement which causes a translational dosing movement of the dosage setting member 9 in the advancing direction.

In the foregoing description, embodiments of the invention, including preferred embodiments have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An administering apparatus, comprising:
   a) a front casing section comprising a reservoir for a product which can be delivered and a first latching element;
   b) a piston which is accommodated in said reservoir such that it can shift in an advancing direction towards a reservoir outlet to deliver product;
   c) a piston rod;
   d) a rear casing section comprising a second latching element which engages with said first latching element to detachably connect the front and rear casing sections;
   e) a drive element which is mounted by said rear casing section such that it can move in and counter to the advancing direction and which acts on said piston rod during a delivery movement in the advancing direction to move said piston in the advancing direction;
   f) and a latching block coupled to said drive element, said latching block comprising a blocking element wherein the blocking element comprises an axially extending body comprising a first end and a second end, the first end comprising a stay projecting at about right angles from the body, the second end comprising a fork around an axial recess, said fork comprising two blocking tongues, and two indentation recesses opposite each other on either side of the second end, wherein the blocking element prevents detachment of the second latching element from the first latching element during delivery of the product until the drive element reaches a releasing position wherein the longitudinally sliding recess is aligned to permit movement of the second latching element into the longitudinally sliding recess to enable detachment of the second latching element from the first latching element.

2. The administering apparatus as set forth in claim 1, wherein the second latching elements is connected to its corresponding casing section such that it can move in a direction transverse to the advancing direction, in order to establish and release the latching engagement.

3. The administering apparatus as set forth in the preceding claim, wherein the second latching element can be moved in a radial direction with respect to a longitudinal axis of said apparatus.

4. The administering apparatus as set forth in claim 2, wherein the second latching element has to be activated, in order to release the latching engagement in the releasing position of the drive element.

5. The administering apparatus as set forth in claim 4, wherein the second latching element is connected to an unlatching button that enables detachment of the second latching element from the first latching element when the drive mechanism is in the releasing position.

6. The administering apparatus as set forth in claim 1, wherein the front casing section and the rear casing section are fixed to each other in and counter to the advancing direction by the latching elements in latching engagement.

7. The administering apparatus as set forth in claim 1, wherein engagement of the second latching element in the first latching element prevents rotational movement between the front and rear casing sections.

8. The administering apparatus as set forth in claim 1, wherein the second latching elements is arranged on the rear casing section such that it can move in and out of latching engagement with the first latching element, and a restoring means acts elastically on the second latching element, in order to prevent the latching engagement from releasing by itself.

9. The administering apparatus as set forth in claim 1, wherein the blocking element and the drive element are coupled such that the drive element slaves said blocking element during the delivery movement.

10. The administering apparatus as set forth in claim 9, wherein the blocking element can be moved transverse to a direction in which one of the latching elements has to be moved in order to release the latching engagement.

11. The administering apparatus as set forth in claim 9, wherein the drive element and the blocking element cannot be moved in and counter to the advancing direction, relative to each other.

12. The administering apparatus as set forth in claim 9, wherein at least one indentation recess only overlaps the second latching element in the releasing position of the drive element, such that said second latching element can be moved at least partially into said indentation recess, in order to release the latching engagement.

13. The administering apparatus as set forth in claim 1, wherein the administering apparatus comprises a dosage setting member which is in dosing engagement with the piston rod, such that it is moved relative to the piston rod in a dosing movement for selecting a product dosage, and moved jointly with the piston rod in the advancing direction relative to the front casing section in a delivery movement for delivering the product.

14. The administering apparatus as set forth in claim 13, wherein said dosage setting member abuts against a delivery stopper of the front casing section in the advancing direction, said delivery stopper limiting the delivery movement in the advancing direction.

15. The administering apparatus as set forth in claim 13, wherein the drive element pushes against the dosage setting member during its delivery movement and thus slaves the piston rod.

16. The administering apparatus as set forth in claim 1, wherein the administering apparatus comprises a dosage setting member which engages with the piston rod such that it can move counter to the advancing direction relative to the front casing section and the piston rod for selecting a product dosage, and moved jointly with the piston rod in the advancing direction relative to the front casing section for delivering the product.

17. The administering apparatus as set forth in claim 1, wherein the drive element is mounted by the rear casing section such that it can also perform a dosing movement, and is coupled to the piston rod such that it slaves the piston rod during the dosing movement.

18. The administering apparatus as set forth in claim 1, wherein a blocking means is provided which engages with the piston rod in order to prevent the piston rod from moving counter to the advancing direction.

19. The administering apparatus as set forth in claim 1, wherein a blocking means is provided which is in a braking engagement with the piston rod which makes it more difficult for the piston rod to move in the advancing direction.

20. The administering apparatus as set forth in claim 1, wherein the front casing section comprises a reservoir part containing the reservoir and a mechanism holder which is connected to said reservoir part such that it cannot be moved relative to the reservoir part with respect to the advancing direction, and which holds the piston rod and comprises the first latching element.

21. The administering apparatus as set forth in claim 1, wherein a cannula of at most 30 gauge or a cannula outside the size specified in ISO 9626 having an outer diameter of a 30 gauge cannula at most, forms an infusing part of the administering apparatus.

22. The administering apparatus as set forth in claim 21, wherein said cannula is a 31 or 32 gauge cannula.

23. The administering apparatus as set forth in claim 1, wherein the piston rod is held by a mechanism holder, secured against rotating.

24. The administering apparatus as set forth in claim 1, further comprising a dosage setting member which completes a rotational dosing movement and a translational dosing movement relative to the front casing section during dosing, while the piston rod remains stationary during the dosing movement.

25. The administering apparatus as set forth in claim 1, wherein the axial recess forms a slot between the two blocking tongues.

26. A drive device for an administering apparatus, which can be detachably connected to a reservoir module of said administering apparatus, wherein said reservoir module comprises a reservoir for a product which can be delivered and a piston accommodated in said reservoir such that it can shift in an advancing direction to deliver the product, said drive device comprising:
   a) a rear casing section of the administering apparatus which can be connected to the reservoir module, and a latching element for establishing a latching engagement with the reservoir module;
   b) a drive element which is mounted by said rear casing section such that it can move back and forth in a longitudinal direction;
   c) and a blocking slider comprising a generally thin, flat main body, which extends axially, the main body comprising a first end and a second end, the first end comprising a stay, which fastens the blocking slider to the drive element, the stay projecting at about right angles from the main body, the second end comprising a fork around an axial recess, said fork comprising at least two blocking tongues, and two indentation recesses positioned closer to the first end than the blocking tongues, wherein the blocking slider prevents detachment of the latching element during delivery of the product until the drive element reaches a releasing position wherein the longitudinally sliding recess is aligned to permit movement of the latching element into the longitudinally sliding recess to enable detachment of the latching element.

27. The drive device of claim 26, wherein a dosage setting member is in dosing engagement with the piston and configured for a dosing movement relative to the piston to select a product dosage, the dosage setting member further being configured for a joint delivery movement with the piston in the advancing direction relative to the reservoir module to deliver the product.

28. The drive device of claim 27, further including a delivery stopper, the dosage setting member abutting against the delivery stopper during delivery movement in the advancing direction, the delivery stopper thus limiting the delivery movement.

29. An administering apparatus, comprising:
   a front casing section comprising a reservoir for a product which can be delivered and a first latching groove;
   a piston which is accommodated in said reservoir such that it can shift in an advancing direction towards a reservoir outlet, in order to deliver product;
   a piston rod;
   a rear casing section comprising a second latching element that engages with the first latching groove to detachably connect the front and rear casing sections;
   a drive element mounted by said rear casing section such that it can move in and counter to the advancing direction and act on the piston rod during a delivery movement in the advancing direction to move the piston in the advancing direction; and
   a latching block coupled to the drive element, the latching block comprising a blocking element comprising an axially extending thin main body comprising a first end and a second end, the first end comprising a stay which fastens the blocking element to the drive element, the stay projecting generally perpendicularly from the main body, the second end comprising two blocking tongues and a longitudinally sliding recess, wherein the blocking element prevents detachment of the second latching element from the first latching groove during delivery of the product until the drive element reaches a releasing position wherein the longitudinally sliding recess is aligned to permit movement of the second latching element into the longitudinally sliding recess to enable detachment of the second latching element from the first latching groove.

30. The administering apparatus as set forth in claim 29, wherein the piston rod is held by a mechanism holder, secured against rotating.

31. The administering apparatus as set forth in claim 29, further comprising a dosage setting member which completes a rotational dosing movement and a translational dosing movement relative to the front casing section during dosing, while the piston rod remains stationary during the dosing movement.

32. The administering apparatus as set forth in claim 29, wherein the longitudinally sliding recess forms a slot between the two blocking tongues.

33. An administering apparatus, comprising:
   a) a front casing section comprising a reservoir for a product which can be delivered and a first latching element;
   b) a piston accommodated in said reservoir such that it can shift in an advancing direction towards a reservoir outlet to deliver product;
   c) a piston rod;
   d) a rear casing section comprising a second latching element which engages with said first latching element to detachably connect the front and rear casing sections;
   e) a drive element carried by said rear casing section such that it can move in and counter to the advancing direction and which acts on said piston rod during a delivery movement in the advancing direction to move said piston in the advancing direction; and
   f) a latching block coupled to said drive element, said latching block comprising an axially extending blocking element wherein the blocking element comprises a thin piece of material comprising a first end and a second end, the first end comprising a stay which fastens the blocking element to the drive element, the stay projecting generally perpendicularly from the thin piece of material between two annular stays axially spaced on an outer surface of the drive element, the second end comprising at least one indentation recess, at least one blocking tongue and an axial recess, wherein the blocking element prevents detachment of the second latching element from the first latching element during delivery of the product until the drive element reaches a releasing position wherein the axial recess is aligned to permit movement of the second latching element into the axial recess to enable detachment of the second latching element from the first latching element.

34. The administering apparatus as set forth in claim 33, wherein the axial recess forms a slot between two blocking tongues.

35. The administering apparatus as set forth in claim 33, wherein the piston rod is held by a mechanism holder, secured against rotating.

36. The administering apparatus as set forth in claim 33, wherein the blocking element is generally plate-shaped.

37. The administering apparatus as set forth in claim 33, further comprising a dosage setting member which completes a rotational dosing movement and a translational dosing movement relative to the front casing section during dosing, while the piston rod remains stationary during the dosing movement.

* * * * *